| United States Patent [19] | [11] Patent Number: 4,532,342 |
| Hoefle et al. | [45] Date of Patent: Jul. 30, 1985 |

[54] N-SUBSTITUTED AMINO ACIDS AS INTERMEDIATES IN THE PREPARATION OF ACYL DERIVATIVES OF 1,2,3,4-TETRAHYDROISOQUINOLINE-3-CARBOXYLIC ACIDS

[75] Inventors: Milton L. Hoefle; Sylvestor Klutchko, both of Ann Arbor, Mich.

[73] Assignee: Warner-Lambert Company, Morris Plains, N.J.

[21] Appl. No.: 386,375

[22] Filed: Jun. 8, 1982

Related U.S. Application Data

[63] Continuation-in-part of Ser. No. 236,397, Feb. 20, 1981, Pat. No. 4,344,949, which is a continuation-in-part of Ser. No. 193,767, Oct. 3, 1980, abandoned.

[51] Int. Cl.$^3$ .......................................... C07C 103/84
[52] U.S. Cl. .......................................... 560/38; 546/2; 546/5; 546/6; 546/84; 546/113; 546/114; 546/145; 546/164; 546/258; 560/22; 560/39; 560/40; 562/443; 562/444; 562/449
[58] Field of Search ..................... 560/38, 39, 22, 40; 562/443, 444, 449

[56] References Cited

U.S. PATENT DOCUMENTS

| | | | |
|---|---|---|---|
| 3,691,169 | 9/1972 | Gray | 546/90 |
| 3,929,830 | 12/1975 | Richter et al. | |
| 4,046,889 | 9/1977 | Ondetti et al. | 424/244 |
| 4,052,511 | 10/1977 | Cushman et al. | 424/274 |
| 4,086,338 | 4/1978 | Cushman et al. | 424/244 |
| 4,091,024 | 5/1978 | Ondetti et al. | |
| 4,105,776 | 8/1978 | Ondetti et al. | 424/274 |
| 4,105,789 | 8/1978 | Ondetti et al. | 260/500.5 H |
| 4,116,962 | 9/1978 | Ondetti et al. | |
| 4,125,604 | 11/1978 | Okamoto et al. | 546/147 |
| 4,128,653 | 12/1978 | Cushman et al. | 424/267 |
| 4,129,566 | 12/1978 | Ondetti et al. | 546/326 |
| 4,140,864 | 2/1979 | Ondetti et al. | 548/344 |
| 4,146,084 | 5/1979 | Ondetti et al. | 546/263 |
| 4,154,840 | 5/1979 | Ondetti et al. | 546/188 |
| 4,154,935 | 5/1979 | Ondetti et al. | 546/189 |
| 4,154,936 | 5/1979 | Ondetti et al. | 546/207 |
| 4,154,942 | 5/1979 | Ondetti et al. | 546/326 |
| 4,251,444 | 2/1981 | Freed et al. | 546/147 |
| 4,256,751 | 3/1981 | Hayashi et al. | 546/147 |
| 4,350,704 | 9/1982 | Hoefle et al. | 424/263 |
| 4,404,206 | 9/1983 | Vincent et al. | 546/147 |

FOREIGN PATENT DOCUMENTS

| | | |
|---|---|---|
| 871574 | 4/1979 | Belgium . |
| 873092 | 6/1979 | Belgium . |
| 12401 | 6/1980 | European Pat. Off. . |
| 12845 | 7/1980 | European Pat. Off. . |
| 18104 | 10/1980 | European Pat. Off. . |
| 18549 | 11/1980 | European Pat. Off. . |
| 24852 | 3/1981 | European Pat. Off. . |
| 31741 | 7/1981 | European Pat. Off. . |
| 0047923 | 3/1982 | European Pat. Off. . |
| 0046953 | 3/1982 | European Pat. Off. . |
| 49605 | 4/1982 | European Pat. Off. . |
| 0049658 | 4/1982 | European Pat. Off. . |
| 0049605 | 4/1982 | European Pat. Off. . |
| 2720966 | 11/1977 | Fed. Rep. of Germany . |
| 2448533 | 9/1980 | France . |
| 2456733 | 12/1980 | France . |
| 5072169 | 5/1980 | Japan . |
| 5127373 | 10/1980 | Japan . |
| 2042535 | 9/1980 | United Kingdom . |

OTHER PUBLICATIONS

Morrison, et al., Organic Chemistry, 2nd Ed., 1966, Allyn and Bacon, Inc., Boston, pp. 733-734.
Patchett et al., "Nature", vol. 288, 1980, pp. 280-283.
Hoefle, et al., "Chemical Abstracts", vol. 96, 1982, col. 96: 122630h.
Hoefle, et al., "Chemical Abstracts", vol. 97, 1982, col. 97: 72257q.
Geiger, et al., "Chemical Abstracts", vol. 97, 1982, col. 92759h.
Neustadt, et al., "Chemical Abstracts", vol. 97, 1982, col. 97: 216730p.
Blankley, "Chemical Abstracts", vol. 98, 1983, col. 98: 54484c.
Kaltenbronn, et al., "Chemical Abstracts", vol. 98, 1983, col. 98: 143072j.

*Primary Examiner*—Glennon H. Hollrah
*Assistant Examiner*—James H. Turnipseed
*Attorney, Agent, or Firm*—Ronald A. Daignault

[57] ABSTRACT

N-substituted amino acids are described which when coupled with 1,2,3,4-tetrahydroisoquinolines result in substituted acyl derivatives of 1,2,3,4-tetrahydroisoquinoline-3-carboxylic acids as anti-hypertensive agents. The novel intermediates are in turn prepared by reacting an amino acid such as alanine with 2-bromo-4-phenyl butanoic acid or an ester thereof.

3 Claims, No Drawings

N-SUBSTITUTED AMINO ACIDS AS INTERMEDIATES IN THE PREPARATION OF ACYL DERIVATIVES OF 1,2,3,4-TETRAHYDROISOQUINOLINE-3-CARBOXYLIC ACIDS

This is a continuation-in-part application of copending U.S. patent application U.S. Ser. No. 236,397, filed Feb. 20, 1981 and now U.S. Pat. No. 4,344,949; which is a continuation-in-part application of copending U.S. patent application U.S. Ser. No. 193,767, filed Oct. 3, 1980, now abandoned.

SUMMARY AND DETAILED DESCRIPTION

The invention relates to substituted acyl derivatives of 1,2,3,4-tetrahydroisoquinoline-3-carboxylic acid compounds having the formula

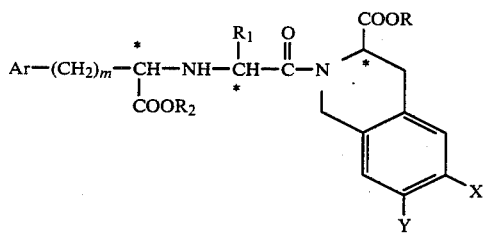

where R is hydrogen, lower alkyl or aralkyl; $R_1$ is hydrogen, lower alkyl, or benzyl; $R_2$ is hydrogen or lower alkyl, and Ar is phenyl or phenyl substituted with 1 or 2 substituents selected from the group consisting of fluorine, chlorine, bromine, lower alkyl, lower alkoxy, hydroxy or amino; X and Y are independently hydrogen, lower alkyl, lower alkoxy, lower alkylthio, lower alkylsulfinyl, lower alkylsulfonyl, hydroxy, or X and Y together are methylenedioxy; m is 0 to 3; and the pharmaceutically acceptable acid salts thereof.

Preferred compounds of the invention are acylated 1,2,3,4-tetrahydroisoquinoline-3-carboxylic acids having the formula

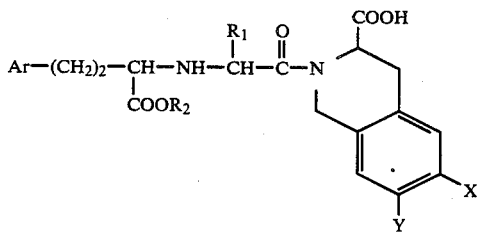

where $R_1$ is hydrogen or lower alkyl containing 1 to 3 carbon atoms, $R_2$ is hydrogen or lower alkyl containing 1 to 3 carbon atoms and Ar is phenyl, and phenyl substituted in the para position by fluorine, chlorine, bromine, methyl, hydroxy, methoxy or amino, x and y are as defined above; and pharmaceutically acceptable acid salts thereof.

Further preferred compounds of the invention are acylated 1,2,3,4-tetrahydroisoquinoline-3-carboxylic acids having the formula

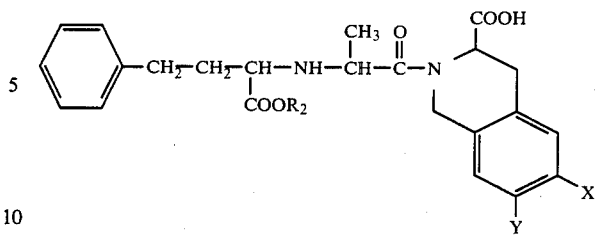

where $R_2$ is hydrogen or lower alkyl containing 1 to 3 carbon atoms X and Y are independently hydrogen or lower alkoxy and pharmaceutically acceptable acid salts thereof; and specifically the compounds designated 2-[2-[(1-carboxy-3-phenylpropyl)amino]-1-oxopropyl]-1,2,3,4-tetrahydro-3-isoquinolinecarboxylic acid; 2-[2-[[1-(ethoxycarbonyl)-3-phenylpropyl]amino]-1-oxopropyl]-1,2,3,4-tetrahydro-3-isoquinolinecarboxylic acid; 2-[2-[(1-carboxy-3-phenylpropyl)amino]-1-oxopropyl]-1,2,3,4-tetrahydro-6,7-dimethoxy-3-isoquinolinecarboxylic acid; 2-[2-[[1-(ethoxycarbonyl)-3-phenylpropyl]amino]-1-oxopropyl]-1,2,3,4-tetrahydro-6,7dimethoxy-3-isoquinolinecarboxylic acid; and pharmaceutically acceptable acid salts thereof.

The terms "lower alkyl" and "lower alkoxy" are intended to mean a straight or branched alkyl group of from one to four carbon atoms.

The compounds of the invention of formula I have asymmetric carbon atoms indicated by asterisks. The 1,2,3,4-tetrahydroisoquinoline-3-carboxylic acid used in this invention has the L (S) configuration. This configuration has been shown to be required for biological activity, and thus active compounds of the invention are derived from either L(−) or DL-1,2,3,4-tetrahydroisoquinoline-3-carboxylic acid.

Optical and diastereo isomers arising from the chirality at the centers marked with an asterisk in formula I and racemates and mixtures thereof are within the scope of this invention. The S configuration at these centers is preferred.

The compounds of the invention may exist in anhydrous form as well as in solvated, including hydrated forms. In general, the hydrated forms and the solvated forms with pharmaceutically acceptable solvents are equivalent to the anhydrous or unsolvated form for the purposes of the invention.

The compounds of the invention of formula I may be prepared from 1,2,3,4-tetrahydroisoquinoline-3-carboxylic acid by first protecting the carboxylic acid group, preferably as an ester, e.g., with a lower alkyl, benzyl or trimethylsilyl group. The protected carboxylic acid compound is coupled to an N-protected amino acid, e.g., glycine or L-alanine, protected on nitrogen with t-butyloxycarbonyl or benzyloxycarbonyl. The coupling is carried out by any of a variety of standard peptide coupling techniques as disclosed, for example, in "The Peptides. Analysis, Synthesis, Biology, Vol. 1 Major Methods of Peptide Bond Formation, Part A", ed. E. Gross, J. Meierhofer, Academic Press N.Y. (1979). An especially useful method involves the use of a dehydrating agent, such as dicyclohexylcarbodiimide alone or in the presence of reagents forming reactive esters, e.g., 1-hydroxybenztriazole, in suitable aprotic solvents such as dimethylformamide, acetonitrile, tetrahydrofuran or chlorinated hydrocarbons. This gives the intermediate (N-protected-2-aminoacyl)-1,2,3,4-tetrahydroisoquinoline-3-carboxylic acid esters. These may then be either partially or totally deblocked depending on the protecting groups chosen, using anhydrous acids, e.g., hydrochloric acid in acetic acid or trifluoroacetic acid in methylene chloride, or hydrogen gas and a catalyst to give the intermediate dipeptide either in free form or protected as an ester.

The compounds of the invention of formula I may then be prepared by reacting the intermediate dipeptide or its ester derivative with α-keto-4-substituted phenylbutyric acid or its lower alkyl ester derivatives under dehydrating and reducing conditions. Preferred dehydrating agents include molecular seives in aprotic solvents and preferred reducing agents include sodium cyanoborohydride or hydrogen gas with a catalyst.

Alternatively, the dipeptide or its ester derivative may be reacted with an -halo-4-substituted phenylbutyric acid or its ester in the presence of a suitable basic reagent, such as triethylamine or alkali carbonates or bicarbonates, in a solvent, to give the compounds of the invention of formula I. Ester protected products may be hydrolyzed under basic or acidic reaction conditions to free acid derivatives, or, in the case of benzyl esters, catalytic hydrogenolysis may be preferred.

Alternately, compounds of the invention of formula I may be prepared in a different manner. This consists of applying either of the two methods described above for the attachment of the 2-(4-phenylbutyric acid) moiety to the protected dipeptide, first to glycine or L-alanine, which may be protected as an ester, to give N-[2-(4-phenylbutyric acid)]-substituted glycine or L-alanine derivative.

After selective deblocking of the acid moiety on the glycine or alanine portion of the product, the resulting monoacid may be coupled, either directly or subsequent to suitable blocking of the amino group, via standard peptide coupling procedures to the 1,2,3,4-tetrahydro-3-isoquinoline carboxylate, protected as an ester. Selective or complete removal of the ester groups and any amine protecting groups yield the compounds of formula I.

The products are obtained typically as a mixture of diastereoisomers which can be separated by standard methods of fractional crystallization or chromatography.

The compounds of this invention form acid salts with various inorganic and organic acids which are also within the scope of the invention. The pharmaceutically acceptable acid addition salts of the compounds of the present invention may be prepared by conventional reactions by reacting the free amino acid or amino ester form of the product with one or more equivalents of the appropriate acid providing the desired anion in a solvent or medium in which the salt is insoluble, or in water and removing the water by freeze drying. The salts of strong acids are preferred. As exemplary, but not limiting, of pharmaceutically acceptable acid salts are the salts of hydrochloric, hydrobromic, sulfuric, nitric, acetic, fumeric, malic, maleic and citric acids.

The action of the enzyme renin on angiotensinogen, a pseudoglobulin in blood plasma, produces the decapeptide angiotensin I. Angiotensin I is converted by angiotensin converting enzyme (ACE) to the octapeptide angiotensin II. The latter is an active pressor substance which has been implicated as the causative agent in various forms of hypertension in various mammalian species, e.g., rats and dogs. The compounds of this invention intervene in the renin->angiotensin I->angiotensin II sequence by inhibiting angiotensin I converting enzyme and reducing or eliminating the formation of the pressor substance angiotensin II, and therefore are useful in reducing or relieving hypertension. Thus by the administration of a composition containing one or a combination of compounds of formula I or pharmaceutically acceptable salts thereof, hypertension in the species of mammal suffering therefrom is alleviated. A single dose, or preferably two to four divided daily doses, provided on a basis of about 0.1 to 100 mg per kilogram per day, preferably about 1 to 50 mg per kilogram per day, is appropriate to reduce blood pressure. The substance is preferably administered orally, but parenteral routes such as subcutaneusly, intramuscularly, intravenously or intraperitonealy can also be employed.

In vitro ACE Assay: Angiotensin converting enzyme (ACE) inhibitory activity was determined by assaying guinea pig serum ACE in the presence and absence of the test compound. ACE from guinea pig serum and the test compounds were preincubated for 10 minutes before the addition of the labelled substrate $^3$H-hippurylglycyl-glycine. After a 60 minute incubation of 37° C. the reaction was stopped by the addition of 0.1N HCl. ACE cleaves the hippuryl-glycyl bond to form the dipeptide glycyl-glycine and $^3$H-hippuric acid. The $^3$H-hippuric acid was then extracted with ethyl acetate and the ACE of a given sample calculated as the amount of $^3$H-hippuric acid generated.

TABLE

Acyl Derivatives of 1,2,3,4-Tetrahydroisoquinoline-3-carboxylic Acids (S,S,S configuration) and their In-Vitro Angiotensin-Converting Enzyme Inhibitory Activity

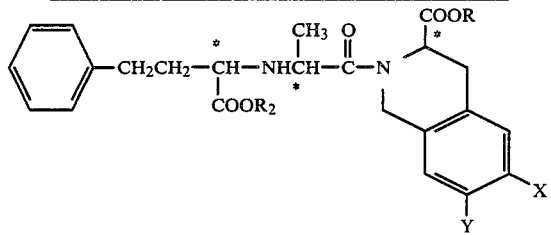

| R | $R_2$ | X | Y | Optical Rotation $[\alpha]_D^{23}$ | ACE I Activity (in vitro) $IC_{50}$ Molar Conc. |
|---|---|---|---|---|---|
| H | Et | H | H | +10.9° (1.0% EtOH)† | $8.3 \times 10^{-9}$ |
| H | Et | $OCH_3$ | $OCH_3$ | +31.6° (1.0% EtOH)† | $5.6 \times 10^{-9}$ |
| H | H | H | H | +14.5° (1.0% MeOH)† | $2.8 \times 10^{-9}$ |
| H | H | $OCH_3$ | $OCH_3$ | +37.8° (1.0% MeOH)† | $3.4 \times 10^{-9}$ |
| $PhCH_2$ | Et | H | H | −11.7° (1.0% MeOH)# | $2.0 \times 10^{-6}$ |
| t-Bu | Et | H | H | +6.4° (2.0% MeOH)# | $3.2 \times 10^{-9}$ |
| $PhCH_2$ | Et | $OCH_3$ | $OCH_3$ | +3.4° (1.0% EtOH)# | $3.0 \times 10^{-7}$ |

† Hydrochloride Salt
Maleate Salt

The compounds of the invention can be utilized to achieve the reduction of blood pressure by formulating in compositions such as tablets, capsules or elixirs for oral administration or in sterile solutions or suspensions for parenteral administration. About 10 to 500 mg of a compound or mixture of compounds of formula I or physiologically acceptable salt thereof is compounded with a physiologically acceptable vehicle, carrier, excipient binder, preservative, stabilizer, flavor, etc., in a unit dosage form as called for by accepted pharmaceutical practice. The amount of active substance in these compositions or preparations is such that a suitable dosage in the range indicated is obtained.

Illustrative of the adjuvants which may be incorporated in tablets, capsules and the like are the following: a binder such as gum tragacanth, acacia, corn starch or gelatin; an excipient such as dicalcium phosphate; a disintegrating agent such as corn starch, potato starch, alginic acid and the like; a lubricant such as magnesium stearate; a sweetening agent such as sucrose, lactose or saccharin; a flavoring agent such as peppermint, oil of wintergreen or cherry. When the dosage unit form is a capsule, it may contain in addition to materials of the above type a liquid carrier such as a fatty oil. Various other materials may be present as coatings or to otherwise modify the physical form of the dosage unit. For instance, tablets may be coated with shellac, sugar or both. A syrup or elixir may contain the active compound, sucrose as a sweetening agent, methyl and propyl parabens as preservatives, a dye and a flavoring such as cherry or orange flavor.

Sterile compositions for injection can be formulated according to conventional pharmaceutical practice by dissolving or suspending the active substance in a vehicle such as water for injection, a naturally occurring vegetable oil like sesame oil, coconut oil, peanut oil, cottonseed oil, etc., or a synthetic fatty vehicle like ethyl oleate or the like. Buffers, preservatives, antioxidants and the like can be incorporated as required.

The invention is illustrated by the following examples.

EXAMPLE 1

2-[2-[[1-(Ethoxycarbonyl)-3-phenylpropyl]amino]-1-oxopropyl]-1,2,3,4-tetrahydro-6,7-dimethoxy-3-isoquinolinecarboxylic Acid, Hydrochloride, Hydrate (S,S,S)

A quantity of 0.0079 mole of the hydrochloride of 2-[2-[[1-(ethoxycarbonyl)-3-phenylpropyl]amino]-1-oxopropyl]-1,2,3,4-tetrahydro-6,7-dimethoxy-3-isoquinolinecarboxylic acid, phenylmethyl ester (S,S,S) dissolved in 100 ml of tetrahydrofuran was catalytically debenzylated with hydrogen and 0.5 g of 20% Pd/carbon at low pressure. The catalyst was filtered off and the product was precipitated as a relatively nonhydroscopic solid by the addition of a 10 fold quantity of ether; wt 3.7 g (88%); mp 120°–140° C.; tlc (20% MeOH-CHCl$_3$/SiO$_2$) one spot, Rf 0.5–0.7; $[\alpha]_D23 = +31.6°$ (1.05% EtOH).

Anal. Calc'd for $C_{27}H_{34}N_2O_7 \cdot HCl \cdot H_2O$: C, 58.63; H, 6.74; N, 5.07. Found: C, 58.59; H, 6.38; N, 5.06.

The noncrystalline diester hydrochloride starting material used above was prepared by treatment of 5.54 g (0.0079 mole) of the maleate salt (prepared by the process of Example 5) with excess saturated sodium bicarbonate, extraction of the free base into 50% ether-ethyl acetate, treatment of this solution with excess hydrogen chloride and concentration at reduced pressure.

EXAMPLE 2

2-[2-[[1-(Ethoxycarbonyl)-3-phenylpropyl]amino]-1-oxopropyl]-1,2,3,4-tetrahydro-3-isoquinolinecarboxylic Acid, Hydrochloride, Hydrate, (S,S,S)

Procedure A: Debenzylation procedure

2-[2-[[1-(Ethoxycarbonyl)-3-phenylpropyl]amino]-1-oxopropyl]-1,2,3,4-tetrahydro-3-isoquinolinecarboxylic acid, phenylmethyl ester, maleate, (S,S,S) (prepared by the procedure of Example 6) was catalytically debenzylated by the procedure set forth in Example 1 to yield the product; mp 105°–120° C.; yield, 56%; tlc (20% MeOH-CHCl$_3$/SiO$_2$) one spot Rf 0.5–0.6; $[\alpha]_D23 = +10.9°$ (1.03% EtOH).

Anal. Calc'd for $C_{25}H_{30}N_2O_5 \cdot HCl \cdot H_2O$: C, 60.90; H, 6.75; N, 5.68. Found: C, 61.00; H, 6.37; N, 5.59.

Procedure B: Via cleavage of 1,1-dimethylethyl ester

A quantity of 100 g of trifluoroacetic acid was added to 11.6 g (0.023 mole) of 2-[2-[[1-ethoxycarbonyl)-3-phenylpropyl]amino]-1-oxopropyl]-1,2,3,4-tetrahydro-3-isoquinolinecarboxylic acid, 1,1-dimethylethyl ester (S,S,S) (prepared by the procedure of Example 7). The mixture was stirred to solution and for one hour at room temperature. Most of the trifluoroacetic acid was removed on the rotary evaporator and the remaining traces were removed by the successive additions and removal by rotary evaporation of 2×50 ml of THF. The residual oil was dissolved in about 400 ml of dry ether and the hydrochloride was precipitated by addition of a solution of 1.0 g (excess) of dry hydrogen chloride dissolved in 20 ml of dry ether. After filtration and washing with dry ether, the filter cake was dissolved in about 250 ml of water. This solution was filtered through celite and freeze-dried to obtain the product as a partial hydrate; 10.0 g (90%); mp 113°–120° C.

Anal. Calc'd for $C_{25}H_{30}N_2O_5 \cdot HCl \cdot \frac{3}{4} H_2O$: C, 61.55; H, 6.70; N, 5.74. Found: C, 61.51; H, 6.49; N, 5.70.

EXAMPLE 3

2-[2-[(1-Carboxy-3-phenylpropyl)amino]-1-oxopropyl]-1,2,3,4-tetrahydro-6,7-dimethoxy-3-isoquinolinecarboxylic Acid, Hydrochloride, Hydrate (S,S,S)

A solution of 0.553 g (0.001 mole) of 2-[2-[[1-(ethoxycarbonyl)-3-phenylpropyl]amino]-1-oxopropyl]-1,2,3,4-tetrahydro-6,7-dimethoxy-3-isoquinolinecarboxylic acid, hydrochloride, hydrate (S,S,S) (prepared by the process of Example 1) in 4 ml (0.004 mole) of 1N sodium hydroxide and 4 ml of methanol was allowed to stand at room temperature for 20 hours. The reaction solution was added to 5 ml of 1N hydrochloric acid and concentrated at reduced pressure. The last amounts of water were removed by two successive additions and removal at reduced pressure of 25 ml portions of ethanol. The organic portion of the residue was dissolved in 0.5 ml of methanol. Chloroform (30 ml) was added and the solution was dried over sodium sulfate, charcoaled, filtered, and concentrated to give 0.45 g product. This amorphous material was dissolved in 20 ml of tetrahydrofuran and 100 ml of ether was added to precipitate a near white solid product; wt 0.4 g; mp 145°–170° C.; yield, 80%; tlc (20% MeOH-CHCl$_3$/SiO$_2$) Rf 0.1; $[\alpha]_D23 = +37.8°$ (1.09% MeOH).

Anal. Calc'd for $C_{25}H_{30}N_2O_7 \cdot HCl \cdot H_2O$: C, 57.19; H, 6.34; N, 5.34. Found: C, 57.17; H, 6.10; N, 5.51.

EXAMPLE 4

2-[2-[(1-Carboxy-3-phenylpropyl)amino]-1-oxopropyl]-1,2,3,4-tetrahydro-3-isoquinolinecarboxylic Acid, Hydrochloride, Hemihydrate (S,S,S)

2-[2-[[1-(Ethoxycarbonyl)-3-phenylpropyl]amino]-1-oxopropyl]-1,2,3,4-tetrahydro-3-isoquinolinecarboxylic acid, hydrochloride, hydrate (S,S,S) was treated by the procedure set forth in Example 3 to yield the product; mp 140°–170° C.; yield, 39%; $[\alpha]_D 23 = +14.5°$ (1.08% MeOH).

Anal. Calc'd for $C_{23}H_{26}N_2O_5 \cdot HCl \cdot \frac{1}{2} H_2O$: C, 60.59; H, 5.97; N, 6.15; Cl, 7.77. Found: C, 60.68; H, 6.04; N, 5.89; Cl, 7.04.

EXAMPLE 5

2-[2-[[1-(Ethoxycarbonyl)-3-phenylpropyl]amino]-1-oxopropyl]-1,2,3,4-tetrahydro-6,7-dimethoxy-3-isoquinolinecarboxylic Acid, Phenylmethyl Ester, Maleate (S,S,S)

A stirred solution of 5.0 g (0.0158 mole) of ethyl α-[(1-carboxyethyl)amino]benzenebutanoate hydrochloride (S,S) (prepared by the process of Example 8) in 200 ml of methylene chloride was treated successively with 1.60 g (0.0158 mole) of triethylamine, 2.14 g (0.0158 mole) of 1-hydroxybenzotriazole, 5.16 g (0.0158 mole) of 1,2,3,4-tetrahydro-6,7-dimethoxy-3-isoquinolinecarboxylic acid, phenylmethyl ester free base (S-form) (prepared by the process of Example 9); and then with 3.26 g (0.0158 mole) of dicyclohexylcarbodiimide in 10 ml of methylene dichloride. Dicyclohexylurea gradually separated. The mixture was allowed to stand at room temperature overnight. Hexane (300 ml) was added and the urea was filtered. The filtrate was washed with 250 ml of saturated sodium bicarbonate, dried over sodium sulfate and concentrated to remove solvent. The viscous residue was triturated with 50 ml of ether and filtered to remove insolubles. The filtrate was concentrated to give 9.2 g (99%) of crude base.

Preparation of maleate salt: A solution of 9.0 g (0.015 mole) of the above crude base in 50 ml of ethyl acetate was treated with a warm (40° C.) solution of 1.86 g (0.016 mole) of maleic acid in 50 ml of ethyl acetate. White crystals separated; wt 7.2 g (65%); mp 139°–141° C.; tlc of base (generated with aq. sodium bicarbonate treatment of the salt and ethyl acetate extraction) showed one spot, Rf 0.7 (EtOAc/SiO$_2$). Recrystallization from ethyl acetate gave pure material of the same mp; $[\alpha]_D 23 = +3.4°$ (1.05% EtOH).

Anal. Calc'd for $C_{34}H_{40}N_2O_7 \cdot C_4H_4O_4$: C, 64.74; H, 6.29; N, 3.98. Found: C, 64.48; H, 6.30; N, 3.99.

EXAMPLE 6

2-[2-[[1-(Ethoxycarbonyl)-3-phenylpropyl]amino]-1-oxopropyl]-1,2,3,4-tetrahydro-3-isoquinolinecarboxylic Acid, Phenylmethyl Ester, Maleate (S,S,S,)

Ethyl α-[(1-carboxyethyl)amino]benzenebutanoate hydrochloride (S,S) (prepared by the process of Example 8) was coupled with 1,2,3,4-tetrahydro-3-isoquinolinecarboxylic acid, phenylmethyl ester free base (S-form) (prepared by the process of Example 10) by the same procedure used in Example 5; yield, 61%; mp 151°–153° C. (recrystallized from ethyl acetate); tlc of base showed one spot, Rf 0.8 (EtOAc/SiO$_2$); $[\alpha]_D 23 = -11.7°$ (1.0% MeOH).

Anal. Calc'd for $C_{32}H_{36}N_2O_5 \cdot C_4H_4O_4$: C, 67.07; H, 6.25; N, 4.35. Found: C, 66.58; H, 6.09; N, 4.25.

EXAMPLE 7

2-[2-[[1-Ethoxycarbonyl)-3-phenylpropyl]amino]-1-oxopropyl]-1,2,3,4-tetrahydro-3-isoquinolinecarboxylic Acid, 1,1-Dimethylethyl Ester (S,S,S)

A mixture of 8.38 g (0.03 mole) of ethyl α-[(1-carboxyethyl)amino]benzenebutanoate (free amino acid) (S,S) (prepared by the process of Example 8), 8.09 g (0.03 mole) of 1,2,3,4-tetrahydro-3-isoquinolinecarboxylic acid, 1,1-dimethylethyl ester hydrochloride (S-form) (prepared by the process of Example 11), 4.05 g (0.03 mole) of 1-hydroxybenzotriazole and 250 ml of THF was cooled in an ice bath to 3°–5° C. With stirring, 3.04 g (0.03 mole) of triethylamine was added, then a solution of 6.92 g (0.0335 mole) of dicyclohexylcarbodiimide in 30 ml of THF was dropped in slowly over 20 minutes. The reaction mixture was stirred at 3°–5° C. for one hour. The ice bath was removed, and the reaction mixture stirred an additional 3 hours. The separated mixture of triethylamine hydrochloride and dicyclohexylurea was removed by filtration and washed with THF. The filtrate was evaporated on the rotary evaporation to remove all volatiles. The resulting gum was dissolved in about 300 ml of ethyl acetate. After filtration through celite the ethyl acetate solution was extracted 2 times with 100 ml of saturated sodium bicarbonate solution, once with 75 ml of 2N citric acid solution, once with 100 ml of saturated sodium bicarbonate solution and once with 100 ml of saturated sodium chloride solution. After drying with anhydrous MgSO$_4$ and filtration, the ethyl acetate was removed on the rotary evaporator to yield 16.9 g of a light brown gum. This gum was dissolved in 350 ml of boiling hexane and decanted through celite. The hexane solution was cooled in ice, seeded and stirred until crystallization was well established. The product was filtered, washed with cold hexane and dried; wt 11.6 g (78%); mp 68.5°–71° C.; $[\alpha]_D 23 = -12.2°$ (2% MeOH). Pure material had mp 71°–72° C.; $[\alpha]_D 23 = -12.6°$ (2% MeOH). The maleate salt had mp 127.5°–128.5° C.; $[\alpha]_D 23 = +46.4$ (2% MeOH).

EXAMPLE 8

Ethyl α-[(1-Carboxyethyl)amino]benzenebutanoate Hydrochloride (S,S)

A solution of 2.0 g of t-butyl alamine (S-form) and 3.78 g of ethyl 2-bromo-4-phenylbutanoate in 25 ml of dimethylformamide was treated with 1.8 ml of triethylamine and the solution was heated at 70° C. for 18 hours. The solvent was removed at reduced pressure and the residue was mixed with water and extracted with ethyl ether. The organic layer was washed with water and dried over magnesium sulfate. Concentration of the solvent at reduced pressure gave the oily t-butyl ester of the intermediate which was found to be sufficiently pure by gas liquid chromatography for further use.

A solution of 143.7 g of this t-butyl ester in 630 ml of trifluoroacetic acid was stirred at room temperature for one hour. The solvent was removed at reduced pressure and the residue was dissolved in ethyl ether and again evaporated. This operation was repeated. Then the ether solution was treated dropwise with a solution of hydrogen chloride gas in ethyl ether until precipitation ceased. The solid, collected by filtration, was a mixture of diastereoisomers, mp 153°–165° C., $[\alpha]_D23 = +3.6°$ (1% MeOH).

In order to separate the preferred S, S isomer, a suspension of 10.0 g of the mixture in 200 ml of methylene chloride was stirred at room temperature for five minutes and filtered; the solid was washed with additional methylene chloride and finally ether. The solid material, mp 202°–208° C. (dec.), $[\alpha]_D23 = -29.3°$ (1% MeOH) was the less preferred diastereoisomer having the R, S configuration (S referring to the portion derived from L-alanine). The preferred S, S diastereoisomer was recovered from the filtrate after concentration and trituration of the residue with ether; mp 137°–139° C.; $[\alpha]_D23 = +31.3°$ (1% MeOH).

The free amino acid (S,S-form) was prepared by treatment of an aqueous solution of the hydrochloride with saturated sodium acetate. The product was filtered, washed efficiently with cold water and recrystallized c from ethyl acetate; mp 149°–151° C.; $[\alpha]_D23 = +29.7°$ (1% 0.1N HCl).

EXAMPLE 9

1,2,3,4-Tetrahydro-6,7-dimethoxy-3-isoquinolinecarboxylic Acid, Phenylmethyl Ester, Hydrochloride (S-form)

A mixture of 1,2,3,4-tetrahydro-6,7-dimethoxy-3-isoquinolinecarboxylic acid, hydrochloride (S-form) and 600 ml of benzyl alcohol was saturated with hydrogen chloride gas. The temperature rose to 45° C. The mixture was stirred at room temperature for three days. A relatively small amount of solid was filtered off and the filtrate was treated with ca 2-liters of ether to precipitate crude product; wt 37.5 g; yield, 83%. Purification was effected by treatment with excess saturated sodium bicarbonate, extraction of base into ethyl acetate and precipitation of hydrochloride salt with HCl gas. Recrystallization from methanol-ether gave pure product; mp 255°–260° C.; $[\alpha]_D23 = -81.3°$ (1.0% MeOH); tlc (20% MeOH-CHCl$_3$/SiO$_2$) one spot Rf 0.8.

Anal. Calc'd for C$_{19}$H$_{21}$NO$_4$·HCl: C, 62.72; H, 6.10; N, 3.85. Found: C, 62.54; H, 5.99; N, 4.00.

EXAMPLE 10

1,2,3,4-Tetrahydro-3-isoquinolinecarboxylic Acid, Phenylmethyl Ester, Hydrochloride (S-form)

Benzyl alcohol, 750 ml, was treated with 150 g of commercial polyphosphoric acid and warmed and stirred at 90° C. to obtain a homogeneous mixture. Solid 1,2,3,4-tetrahydro-3-isoquinolinecarboxylic acid (S-form) 65.2 g was added. The mixture was stirred 4 hours at 95°–105° C. and then allowed to stand at room temperature for 18 hours. A solution of 18.5 g gaseous hydrochloric acid in 2.5 of anhydrous ether was added, and the product separated slowly on cooling overnight. Filtration gave the crude benzyl 1,2,3,4-tetrahydro-3-isoquinoline carboxylate hydrochloride. This was purified by recrystallization from ethanol twice to give material with mp 190.5°–191° C.; $[\alpha]_D23 = -83.3°$ (1% 1:1 methanol/1N hydrochloric acid).

EXAMPLE 11

1,2,3,4-Tetrahydro-3-isoquinolinecarboxylic Acid, 1,1-Dimethylethyl Ester Hydrochloride (S-form)

This compound was prepared by passing 447 g of isobutylene into a 0° C. solution of 63.5 g of 1,2,3,4-tetrahydro-3-isoquinoline carboxylic acid (S-form) in 650 ml of dry dioxane and 65 ml of concentrated sulfuric acid under nitrogen. The reaction vessel was sealed and shaken for 17 hours at room temperature. The reaction vessel was vented and the mixture was poured into 25 of cold 2N sodium hydroxide. The product is extracted into ether. The ether solution was washed with water, dried, and concentrated to about 500 ml. This was treated with excess 6N isopropanolic hydrochloric acid to precipitate the product, which was collected by filtration. A sample purified by recrystallization from ethanol/ether had mp 190°–192° C. (dec.), $[\alpha]_D23 = -88.7°$ (2% MeOH).

EXAMPLE 12

A quantity of 1000 tablets each containing 100 mg of 2-[2-[[1-(ethoxycarbonyl)-3-phenylpropyl]amino]-1-oxopropyl]-1,2,3,4-tetrahydro-6,7-dimethoxy-3-isoquinolinecarboxylic acid, hydrochloride, hydrate (S,S,S) is produced from the following ingredients:

| | |
|---|---|
| 2-[2-[[1-(Ethoxycarbonyl)-3-phenylpropyl]-amino]-1-oxopropyl]1,2,3,4-Tetrahydro-6,7-dimethoxy-3-isoquinolinecarboxylic acid, hydrochloride hydrate (S,S,S) | 100 g |
| Corn starch | 50 g |
| Gelatin | 7.5 g |
| Avicel (microcrystalline cellulose) | 25 g |
| Magnesium stearate | 2.5 g |

2-[2-[[1-(Ethoxycarbonyl)-3-phenylpropyl]amino]-1-oxopropyl]-1,2,3,4-tetrahydro-6,7-dimethoxy-3-isoquinolinecarboxylic acid, hydrochloride, hydrate (S,S,S) and corn starch are admixed with an aqueous solution of the gelatin. The mixture is dried and ground to fine powder. The Avicel and then the magnesium stearate are admixed with the granulation. This is then compressed in a tablet press to form 1000 tablets each containing 100 mg of active ingredients.

EXAMPLE 13

A quantity of 1000 tablets each containing 200 mg of 2-[2-[[1-(ethoxycarbonyl)-3-phenylpropyl]amino]-1-oxopropyl]-1,2,3,4-tetrahydro-6,7-dimethoxy-3-isoquinolinecarboxylic acid, hydrochloride, hydrate (S,S,S) is produced from the following ingredients:

| | |
|---|---|
| 2-[2-[[1-(Ethoxycarbonyl)-3-phenylpropyl]-amino]-1-oxopropyl]-1,2,3,4-tetrahydro-6,7-dimethoxy-3-isoquinolinecarboxylic acid, hydrochloride, hydrate (S,S,S) | 200 g |
| Lactose | 100 g |
| Avicel | 150 g |
| Corn starch | 50 g |
| Magnesium stearate | 5 g |

The 2-[2-[[1-(Ethoxycarbonyl)-3-phenylpropyl]-amino]-1-oxopropyl]-1,2,3,4-tetrahydro-6,7-dimethoxy-3-isoquinolinecarboxylic acid, hydrochloride, hydrate (S,S,S) lactose and Avicel are admixed, then blended with the corn starch. Magnesium stearate is added. The dry mixture is compressed in a tablet press to form 1000, 505 mg tablets each containing 200 mg of active ingredient. The tablets are coated with a solution of Methocel E 15 (methyl cellulose) including as a color a lake containing yellow No. 6.

EXAMPLE 14

Two piece No. 1 gelatin capsules each containing 250 mg of 2-[2-[[1-(ethoxycarbonyl)-3-phenylpropyl]-amino]-1-oxopropyl]-1,2,3,4-tetrahydro-6,7-dimethoxy- 3-isoquinolinecarboxylic acid, hydrochloride, hydrate (S,S,S) are filled with a mixture of the following ingredients:

| | |
|---|---|
| 2-[2-[[1-(Ethoxycarbonyl)-3-phenylpropyl]-amino]-1-oxopropyl]-1,2,3,4-tetrahydro-6,7-dimethoxy-3-isoquinolinecarboxylic acid, hydrochloride, hydrate (S,S,S) | 250 mg |
| Magnesium stearate | 7 mg |
| USP lactose | 193 mg |

EXAMPLE 15

An injectable solution is produced as follows:

| | |
|---|---|
| 2-[2-[[1-(Ethoxycarbonyl)-3-phenylpropyl]-amino]-1-oxopropyl]-1,2,3,4-tetrahydro-6,7-dimethoxy-3-isoquinolinecarboxylic acid, hydrochloride, hydrate (S,S,S) | 500 g |
| Methyl paraben | 5 g |
| Propyl paraben | 1 g |
| Sodium chloride | 25 g |
| Water for injection q.s. | 5 l |

The active substance, preservatives and sodium chloride are dissolved in 3 liters of water for injection and then the volume is brought up to 5 liters. The solution is filtered through a sterile filter and aseptically filled into presterilized vials which are then closed with presterilized rubber closures. Each vial contains 5 ml of solution in a concentration of 100 mg of active ingredient per ml of solution for injection.

We claim:

1. The N-substituted amino acid according to the formula

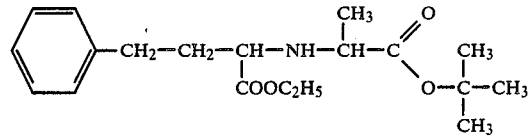

and salts thereof.

2. The N-substituted amino acid according to the formula

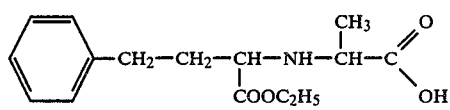

and the hydrochloride salt thereof.

3. The N-substituted amino acid according to claim 2 designated ethyl α-[(1-carboxyethyl)amino]-benzenebutanoate hydrochloride (S,S).

* * * * *